United States Patent [19]  [11] Patent Number: 5,065,740
Itoh  [45] Date of Patent: Nov. 19, 1991

[54] ULTRASONIC MEDICAL TREATMENT APPARATUS

[75] Inventor: Ayao Itoh, Yokohama, Japan

[73] Assignee: Kabushiki Kaisha Toshiba, Kawasaki, Japan

[21] Appl. No.: 555,826

[22] Filed: Jul. 23, 1990

Related U.S. Application Data

[63] Continuation of Ser. No. 137,435, Dec. 23, 1987, abandoned.

[30] Foreign Application Priority Data

Dec. 26, 1986 [JP] Japan .................. 61-315594

[51] Int. Cl.⁵ ............................................ A61B 17/22
[52] U.S. Cl. ............................ 128/24 EL; 128/660.04
[58] Field of Search ......... 128/24 EL, 660.03, 660.04, 128/660.08, 660.09, 661.01; 606/128

[56]  References Cited

U.S. PATENT DOCUMENTS

| | | | |
|---|---|---|---|
| 4,431,007 | 2/1984 | Amazeen et al. | 128/660.04 |
| 4,455,872 | 6/1984 | Kossoff et al. | 128/660.09 |
| 4,463,763 | 8/1984 | Koyano et al. | 128/660.04 |
| 4,526,168 | 7/1985 | Hassler et al. | 128/328 |
| 4,617,931 | 10/1986 | Dory | 128/328 |
| 4,681,120 | 7/1987 | Kunii | 128/660.08 |
| 4,757,820 | 7/1988 | Itoh | 128/660.03 |
| 4,771,787 | 9/1988 | Wurster et al. | 128/328 |
| 4,787,393 | 11/1988 | Fukukita et al. | 128/660.04 |
| 4,787,394 | 11/1988 | Ogura | 128/660.03 |
| 4,958,639 | 9/1990 | Uchiyama et al. | 128/660.03 |

FOREIGN PATENT DOCUMENTS 0035215 9/1981 European Pat. Off. ....... 128/660.04
3328068 2/1985 Fed. Rep. of Germany ...... 128/328

OTHER PUBLICATIONS

Ito et al., C-Mode Scan and Resolution Improvement Technique for Ultrasonic Diagnosis, IEEE Trans Bio ENG, vol. BME-26, No. 1 (Jan. 1979).
Ito, Ken-ichi et al., A New Real-Time Ultrasonic Diagnostic System for Dynamic and Still Images, SEE (Japan), No. 144, Dec. 1978.

Primary Examiner—Francis Jaworski
Assistant Examiner—Scott R. Akers
Attorney, Agent, or Firm—Oblon, Spivak, McClelland, Maier & Neustadt

[57]  ABSTRACT

An ultrasonic medical treatment apparatus contains a medical treatment ultrasonic transducer and an image ultrasonic transducer which is mechanically movable. The image ultrasonic transducer provides tomographic data to obtain, based on an arithmetic operation, one or both of plural pieces of tomographic data (B-mode tomogram) representing a first plane of a region of interest, extending parallel to the direction of ultrasonic wave propagation, and plural pieces of tomographic data (C-mode tomogram) representing a second plane intersecting with the first plane at right angles. These pieces of tomographic data are displayed by a display, so that an operator can recognize three-dimensional tomographic data from the displayed pieces of tomographic data, and ensuring an exact medical treatment of the region of interest.

5 Claims, 5 Drawing Sheets

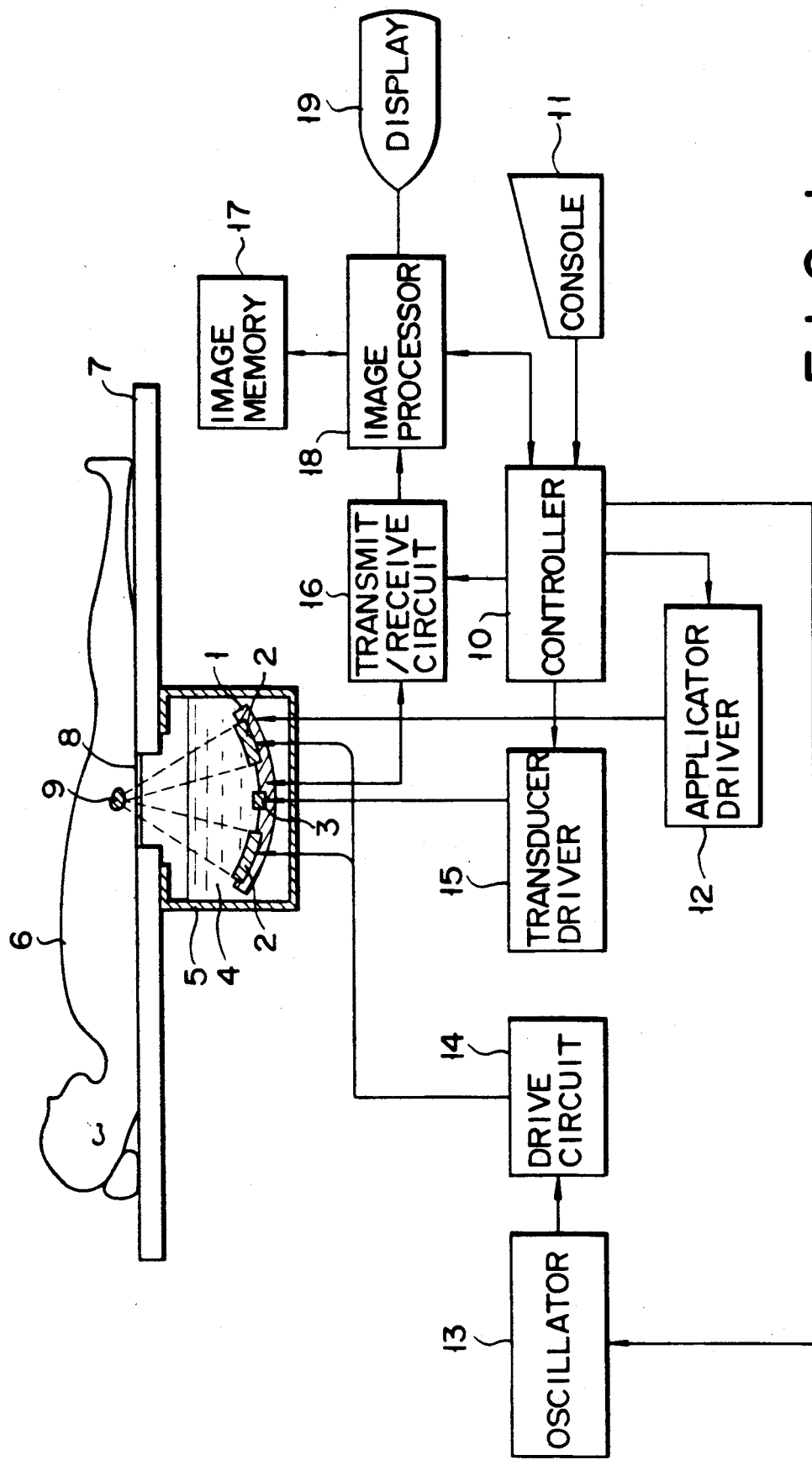
F I G. 1

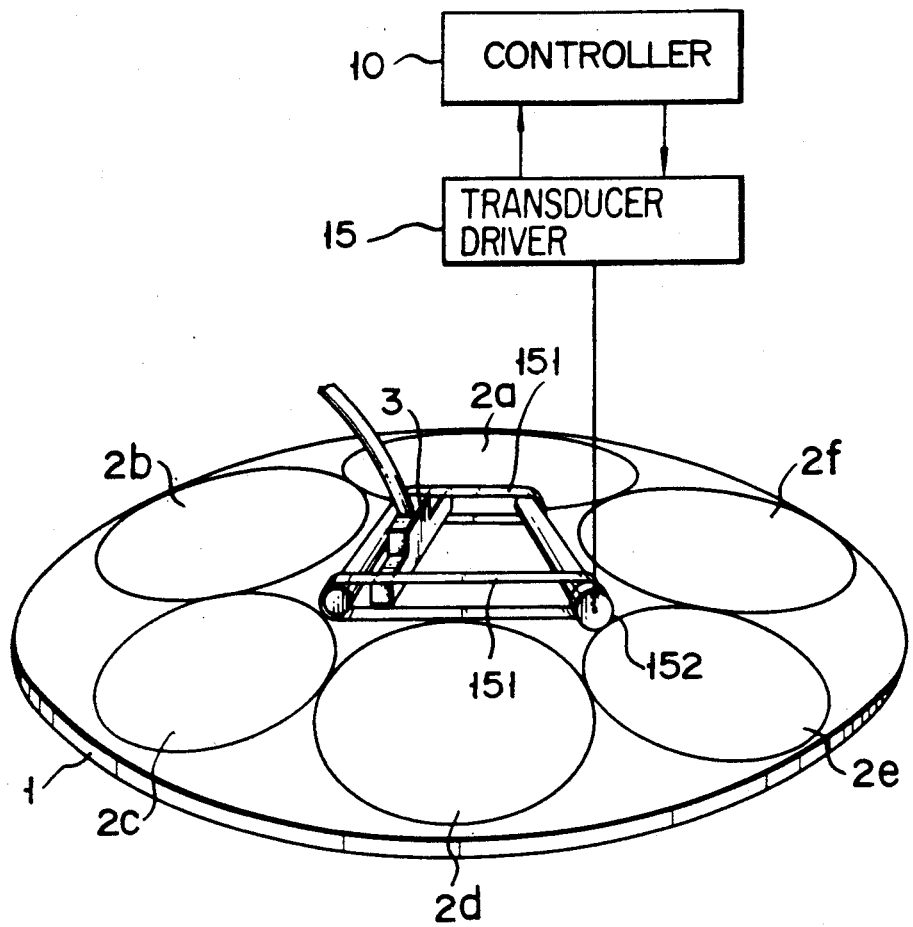
F I G. 4
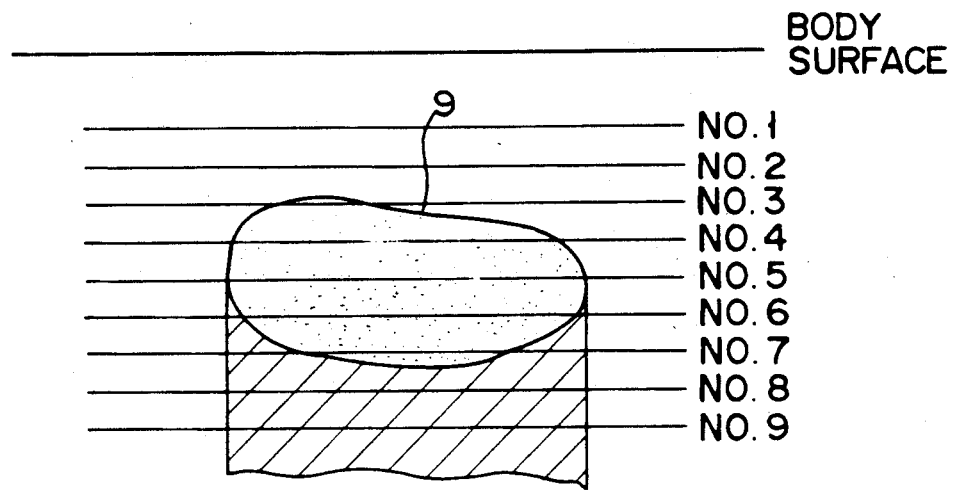
F I G. 5

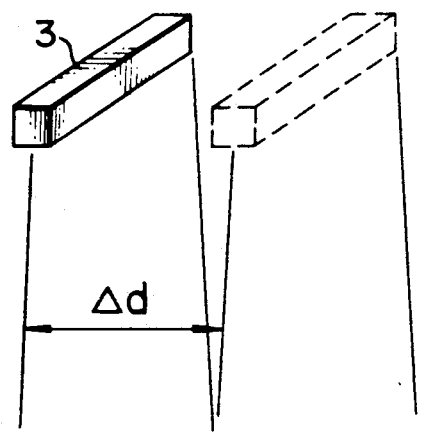
F I G. 8A
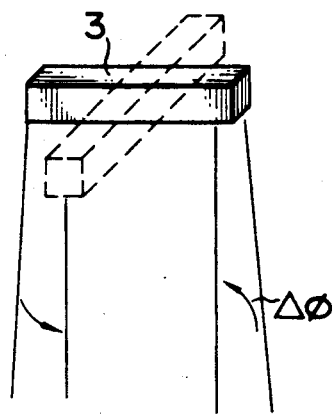
F I G. 8B
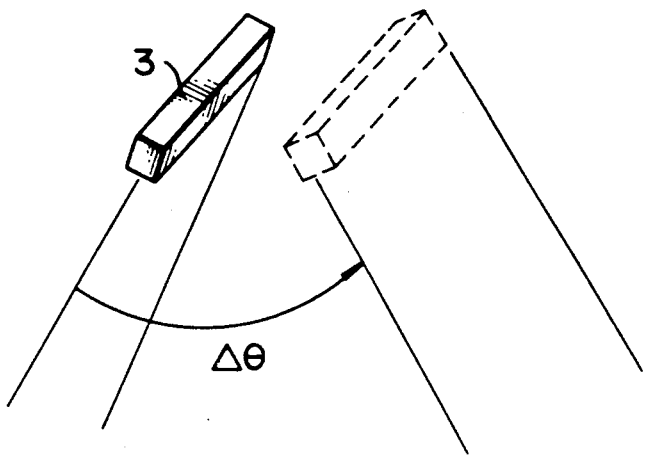
F I G. 8C

ULTRASONIC MEDICAL TREATMENT APPARATUS

This application is a continuation of application Ser. No. 07/137,435 filed on Dec. 23, 1987, now abandoned.

BACKGROUND OF THE INVENTION

This invention relates to an ultrasonic medical treatment apparatus for use in medical treatment of patients, by radiating ultrasonic waves onto the location of a calculus or tumor within the patient's body, and, more particularly, to an ultrasonic medical treatment apparatus which generates three-dimensional image data to enlarge a field of the region of interest of the patient to be treated.

Most importantly, an ultrasonic treatment apparatus must be able to focus ultrasonic waves precisely on the region of interest (ROI) and to radiate it with ultrasonic waves. A prior art of this invention is U.S. Pat. No. 4,617,931. In this patent, a probe for the B-mode is located at the center of the group of ultrasonic therapeutic transducers to obtain the image of only the tomogram extending in the direction of the depth of the patient's body, i.e., the B-mode tomogram. While seeing the tomogram, an operator monitors the ROI and positions the medical treatment ultrasonic transducer. If breathing or movement of the body occurs when using the prior art apparatus, correction of the moved ROI location must be performed and is a troublesome operation. Further, when the body movement is great, the ROI may go out of the field of view. In this case, it is very difficult to obtain the ROI and to set it within the field. The prior art contains examples of apparatus which are able to monitor a ROI in a three-dimensional manner. Such an apparatus uses B-mode probes arranged such that their scanning surfaces are orthogonal to each other. An improved apparatus of this type is disclosed in Japanese Patent Disclosure No. 59-101143. This apparatus can obtain at least two ultrasonic B-mode tomographic images arranged orthogonally. By using a main beam, whose position against either of those images is known precisely, a ROI whose position varies with time can be traced continuously, in a three-dimensional manner and in real time, even when the region of interest varies with the passage of time. In the prior art, for example, when the body moves and the position to be treated moves accordingly, the movement of the position can be detected at any moment by the two B-mode probes, but the field is narrow, and when the ROI is once out of the field, it is very difficult to find it again.

SUMMARY OF THE INVENTION

With the aim of overcoming the above-mentioned disadvantages, this invention has as an object to provide an ultrasonic medical treatment apparatus which can display a plurality of tomograms to recognize a three-dimensional image. Therefore, the apparatus can locate the object in the ROI, within the field of the tomogram, so that an operator can recognize a three-dimensional image, even if the patient moves, and the operator can easily recognize and treat the object even the ROI is gone out of the field because when the ROI is out of the image field, the image field can be moved to again contain the ROI because when the ROI is out of the image field, the image field can be moved to again contain the ROI.

To achieve the above object, there is provided an ultrasonic medical treatment apparatus comprising medical treatment ultrasonic transducer means, image ultrasonic transducer means for imaging and providing the tomographic data representing a plurality of tomograms as three-dimensional data of a ROI in which an object is located to be treated, means for mechanically moving said imaging ultrasonic transducer means, and display means for displaying said plurality of tomographic data.

With such an arrangement, the ultrasonic medical treatment apparatus, according to this invention, can detect an object located in a ROI in the form of three-dimensional image and can treat the object. Therefore, the ROI can be found within the field of the tomogram, in the form of three dimensional image, even if the patient moves, by mechanically driving the imaging ultrasonic transducer. Even when the ROI is out of the field, it can be detected again because when the ROI is out of the image field, the image field can be moved to again contain the ROI. Hence, ultrasonic waves can be applied from the ultrasonic transducer to, and focused at, the ROI thereby to treat an object in the ROI.

BRIEF DESCRIPTION OF THE DRAWINGS

FIG. 1 shows a block diagram of an arrangement of an ultrasonic medical treatment apparatus according to an embodiment of this invention, an ultrasonic applicator of the apparatus being taken on line I—I in FIG. 2 and viewed in the direction of arrows;

FIG. 4 shows a block diagram of an arrangement of a transducer drive section as is shown in FIG. 1;

FIG. 5 is a B-mode tomogram of a calculus located in a ROI;

FIGS. 8A to 8C show views illustrating three different movements of the image ultrasonic transducer.

DETAILED DESCRIPTION OF THE PREFERRED EMBODIMENTS

A preferred embodiment of an ultrasonic medical treatment apparatus according to this invention will be described referring to the accompanying drawings.

Figure 2:
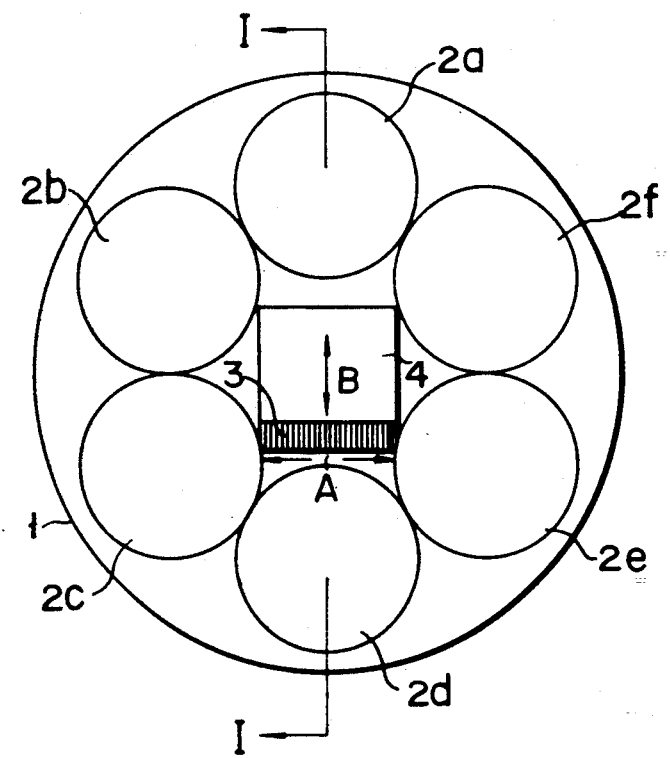
FIG. 2 shows a plan view of an array of ultrasonic transducers for medical treatment and for images, which are arrayed in the ultrasonic applicator as is shown in FIG. 1.

In FIG. 1, there is shown a calculus destroying apparatus as an ultrasonic medical treatment apparatus according to this invention. As is shown, a plurality of circular transducers 2 and a single image ultrasonic transducer 3 are disposed on a circular ultrasonic applicator 1. These are disposed in bath 5, containing water 4. Bath 5 is mounted on the underside of bed 7, on which patient 6 is laid. Bed 7 is opened at the location where bed 7 is coupled with the top end of bath 5, as is shown. Silicon film 8, for example, is stretched covering this opening. Medical treatment ultrasonic transducer 2 transmits ultrasonic waves to the ROI, thereby to treat an object existing in the ROI. The plurality of circular transducers $2a$ to $2f$, as disposed on ultrasonic applicator 1, have each an inwardly curved surface, and are arrayed in a circle with respect to the axis of applicator 1, as is shown in FIG. 2. Image ultrasonic transducer 3, of the linear array type, is disposed at the center of ultrasonic applicator 1 around which circular transducers 2a to 2f are disposed. In this embodiment, the diameter of each of circular transducers 2a to 2f is approximately 100 mm. The array length of image ultrasonic transducer 3 is approximately 70 mm. The diameter of applicator 1 is approximately 350 mm.

The transducer 3 can electronically linear-scan the ROI in the direction of arrow A. Additionally, it can mechanically make the scan in the direction of arrow B. The circular transducers 2a to 2f, are coupled with oscillator 13 through drive circuit 14, as is shown in FIG. 1. Controller 10 is coupled with the related sections of the apparatus, to be described later, and controls them in response to a command from console 11. Applicator driver 12 controls the position of applicator 1 with respect to the ROI. Transducer driver 15 mechanically drives image ultrasonic transducer 3.

Figure 3:
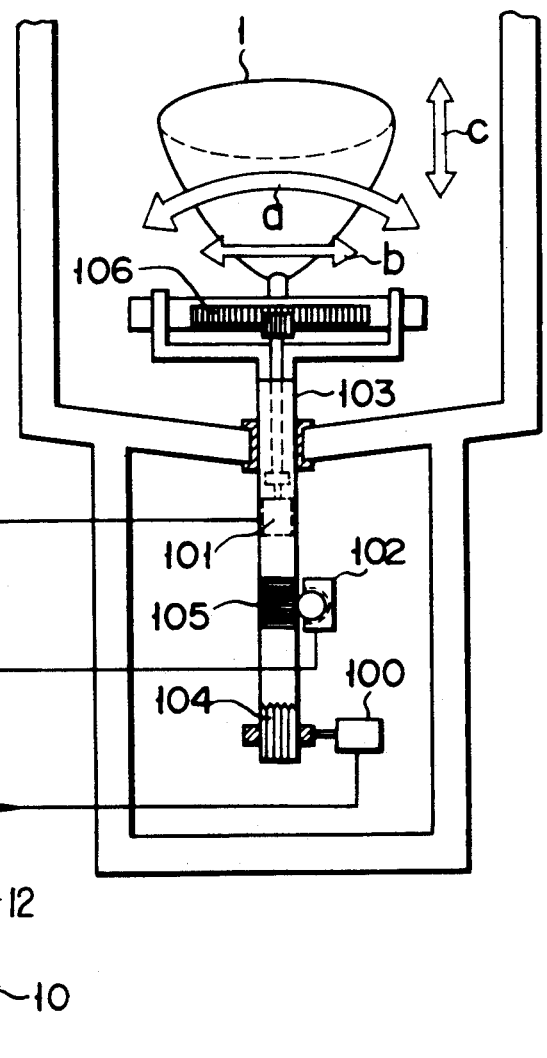
FIG. 3 shows a view illustrating an arrangement of an applicator drive section as is shown in FIG. 1.

Applicator driver 12 is driven by a command supplied from controller 10, as is shown in FIG. 3. Applicator driver 12 outputs a signal representing motor drive information. First to third-pulse motors 100, 101 and 102 are driven by the output signal from driver 12. These motors are supported by shaft 103. The rotations of these motors are transferred to applicator 1, via gear mechanisms 104, 105 and 106, respectively. When first-pulse motor 100 is driven, applicator 1 is rotated in the direction of "a". When second pulse motor 101 is driven, applicator 1 is moved in the direction of "b". When third-pulse motor 102 is driven, applicator 1 is moved in the direction of depth, i.e., "c". In transducer driver 15, as is shown in FIG. 4, belt 151 is wrapped around a pair of shafts, with transducer 3 fixed to belt 151. Shafts 151 are driven by motor 152, so that the transducer 3 is moved. Motor 152 is driven by the output signal from transducer driver 15, and driver 15 is driven by a command from controller 10.

The transmit/receive circuit 16 causes image ultrasonic transducer 3 to electronically scan, and transfer the data, as obtained by the electronic scanning, to image processor 18. Image processor 18 processes the signal from transmit/receive circuit 16, transfers the processed signal to image memory 17, and stores it into the memory. Display 19 receives the data from image processor 18, or reads out the data stored in image memory 17, and displays the tomogram formed from this data.

The operation of the ultrasonic apparatus according to this invention will be described in detail.

To start with, an operator inputs an image collecting command to controller 10. Controller 10 controls transmit/receive circuit 16 and causes image ultrasonic transducer 3 to supply drive pulses. The transducer 3 performs linear scanning in the direction of arrow A as in FIG. 2. When the first linear scanning is completed, the transducer 3 is translated in the direction B from the scanning end position, for approximately 0.5 mm to 0.6 mm, under control of controller 10. After this translation, the linear scanning is performed again. The linear scanning and the translation are alternately repeated, until space 4 is entirely scanned.

After image ultrasonic transducer 3 has performed the linear scanning in the direction of arrow A, transmit/receive circuit 16 collects the information of a tomogram of ROI 9 (referred to as a B-mode image) from the ultrasonic waves reflected from ROI 9, as is shown in FIG. 5, and converts these waves into electrical signals forming image data. The image data is transferred to image processor 18 and then stored into image memory 17. A plurality of B-mode images, as collected by the repeated linear scannings and stored into image memory 17, are read out from the memory and displayed by display 19. ROI 9 can be treated as three-dimensional image data, by using these B-mode tomograms.

Figure 6:
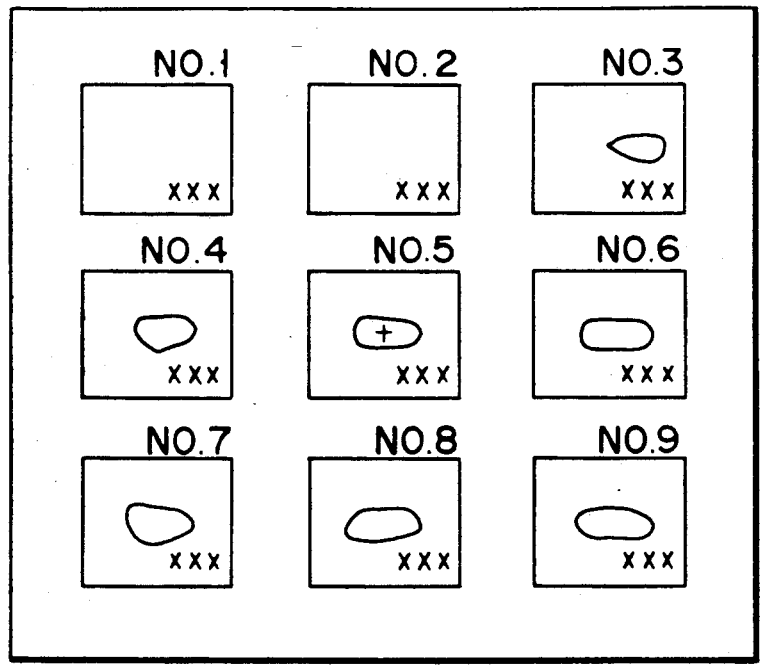
FIG. 6 shows a view illustrating a plurality of C-mode tomograms displayed by a display section.

In response to the drive command from driver 15, image ultrasonic transducer 3 is moved in the direction orthogonal to the B-mode tomographic surface, i.e., in the direction of B (FIG. 2), thereby to obtain a C-mode tomogram i.e., an image of a selected plane perpendicular to the plane of a B-mode tomogram. A plurality of tomograms can be obtained at different depths. For example, the C-mode tomograms at the depths Nos. 1 to 9 can be displayed on the screen, with images Nos. 1 to 9, as is shown in FIG. 6. In the figure, symbol "xxx" in each display indicates a distance from the body surface in "cm" unit. By using the C-mode tomograms thus displayed, ROI 9 can be treated as three-dimensional image information.

As described above, the three dimensional image information of ROI 9 can be obtained only from the plurality of B-mode tomograms and the plurality of C-mode tomographs. Specifically, these B and C-mode tomograms are received by transmit/receive circuit 16, processed by image processor 18, and stored into image memory 17. The tomograms read from memory 17 are displayed by display 19, in the form of a three-dimensional image.

To treat the object, applicator 1 is positioned in accordance with the drive command supplied from applicator driver 12. An operator first checks the position of the ROI while observing the C-mode tomograms on display 19. A marker (+) (No. 5 of FIG. 6) is displayed at a position in the C-mode tomogram, which corresponds to the focal point of medical treatment ultrasonic transducer 2. The operator checks the location of the ROI 9 while observing the C-mode tomogram. The operator operates console 11 to control applicator driver 12 through control 10, thereby locating the ROI 9 at the focal point of medical treatment ultrasonic transducer 2. After checking the ROI, the data of the C-mode tomogram at that location is stored in image memory 17. The operator operates console 11 to drive controller 10, causing oscillator 13 to oscillate.

Figure 7:
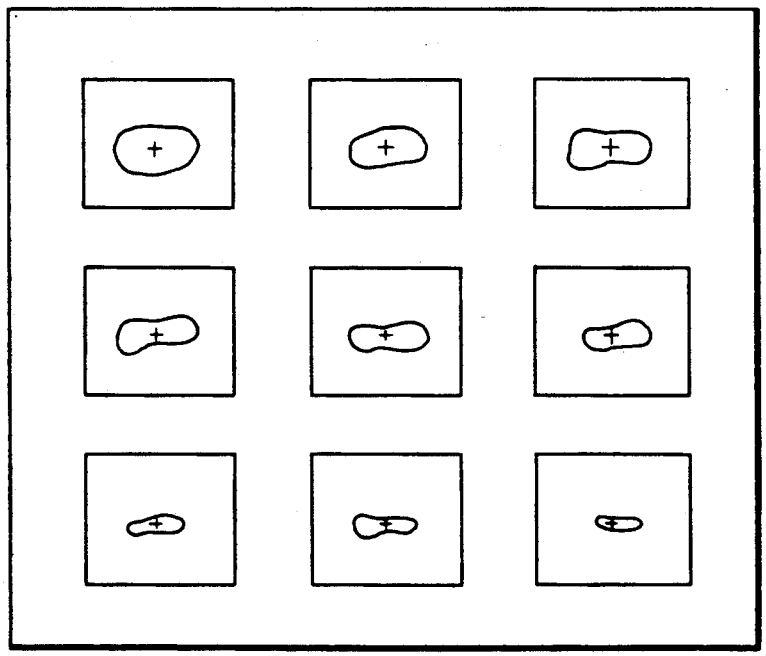
FIG. 7 shows a view illustrating another display of the display section, the display containing a plurality of tomograms which include the focus point of ultrasound for treatment.

Upon receipt of the output of oscillator 13, driver 14 outputs a drive command to medical treatment ultrasonic transducer 2. As a result, the ultrasonic waves from transducer 2 are focused at the ROI 9. The radiation is continued until the calculus is destroyed. The tomographic plane of the ROI 9 under medical treatment changes with time. As is shown in FIG. 7, a plurality of C-mode tomograms is displayed in display 19. The operator can know how the medical treatment proceeds, from these displayed tomograms. These C-mode tomograms are displayed by display 19. They can be displayed sequentially or intermittently, because the image data collected by image ultrasonic transducer 3 is stored in image memory 17. Even when the patient moves, or the calculus moves during the medical treatment, and the ROI 9 shifts from the focal point of the medical treatment ultrasonic transducer 2, the operator can see this on the display 19 at a glance. If necessary, the operator needs only to position the applicator 1 again. Further, if the ROI is out of the field, it can be easily detected and treated. The ultrasonic medical treatment apparatus according to this invention is not limited to the above-mentioned embodiment. Various changes and modifications can be made within the scope of the invention. For example, the linear electronic scanning by linear array transducer for obtaining the tomogram data, which is used in the above-mentioned embodiment, may be replaced by the mechanical scanning, such as sector scanning. In this instance, the image ultrasonic transducer can be small enough to be mounted on applicator 1. Image ultrasonic transducer 3 is translated as is shown in FIG. 8A, in the above-mentioned embodiment. Alternatively, transducer 3 may be swung with respect to the shaft of the transducer in a sector fashion, as is shown in FIG. 8C. As another alternative, it may be rotated in a plane, as is shown in FIG. 8B. Further, applicator 1 may be manually positioned. Alternatively, the position of the ROI is detected, and it is automatically located. For example, if the calculus location or region in each tomographic plane is determined, the apparatus calculates the distance and direction of the focal point. The calculus location may be checked by detecting a level above an echo threshold level or by specially differentiating the image to extract a contour of the image. The medical treatment ultrasonic transducer 2 is arranged such that a plurality of circular transducers are arrayed in a circle, in the abovementioned embodiment. If necessary, other types of transducers may be used, such as annular array transducers in which ring like vibrators are arrayed in a circle, surrounding an axis.

What is claimed is:

1. An ultrasonic medical treatment apparatus comprising:

ultrasonic transistor means having a plurality of transducers arranged in a circuit, for radiating and focusing strong ultrasonic waves on a region of interest within an object to be treated;

image ultrasonic transducer means surrounded by said plurality of transducers, for providing tomographic image data representing a plurality of tomographic planes of the region of interest so than an operator can recognize the tomograms as a three-dimensional image data, said tomographic image data representing a plurality of tomograms of B-mode representing a first tomographic plane of the object in a direction of strong ultrasonic wave propagation and a plurality of tomograms of C-mode representing a second tomographic plane of the object in a direction perpendicular to the first tomographic plane;

means connected to said image ultrasonic transducer means, for mechanically moving said image ultrasonic transducer means;

control means connected to said image ultrasonic transducer means, for processing the tomographic image data supplied from said image ultrasonic transducer means and for detecting a position data corresponding to the region of interest within an object by scanning said image ultrasonic transducer means;

image memory means, connected to said control means for storing the tomographic image data and the position data from said control means;

image processing means connected to said control means and said image memory means and for processing the image data and the position data and for reconstructing the plurality of tomograms of C-mode in a direction perpendicular to the tomograms of B-mode; and display means connected to said image processing means for displaying a plurality of said tomographic image data and said position data read out from said image memory means so that an operator can recognize the three-dimensional image data from the tomograms dispelled thereon.

2. An ultrasonic medical treatment apparatus according to claim 1, wherein said control means for processing the tomographic image data includes:

transmit/receive circuit means for causing said image ultrasonic transducer means performing electronic scanning and transmitting image data obtained from the scanning;

image process means, connected to said transmit/receive circuit means and said image memory means, for processing the image data from said transmit/receive circuit means and transmitting the processed image data to said image memory means thereby to be stored therein; and controller means, connected to said transmit/receive circuit means and said image processor means, for processing the tomographic image data supplied from said image ultrasonic transducer means.

3. The apparatus according to claim 1, wherein said display means displays said first and second tomographic planes, with respective desired positions of said planes displayed thereon simultaneously corresponding to the region of interest within an object.

4. The apparatus according to claim 1, wherein said display means simultaneously displays a plurality of tomograms of different tomographic planes so that an operator can recognize the tomograms as three-dimensional data.

5. The apparatus according to claim 1, wherein said display means simultaneously displays a plurality of tomograms obtained by scanning the same plane at different times so that an operator can recognize the tomograms as three-dimensional data.

* * * * *